(12) United States Patent
Weiskopf et al.

(10) Patent No.: US 11,780,931 B2
(45) Date of Patent: *Oct. 10, 2023

(54) CD47 TARGETED THERAPIES FOR THE TREATMENT OF INFECTIOUS DISEASE

(71) Applicants: The Board of Trustees of the Leland Stanford Junior University, Stanford, CA (US); The United States of America, as represented by the Secretary, Department of Health and Human Services, Bethesda, MD (US); The Regents of the University of California, Oakland, CA (US)

(72) Inventors: Kipp Andrew Weiskopf, Brookline, MA (US); Kim J. Hasenkrug, Victor, MT (US); Cheryl A. Stoddart, Pacifica, CA (US); Joseph McCrary McCune, San Francisco, CA (US); Irving L. Weissman, Stanford, CA (US)

(73) Assignees: The Board of Trustees of the Leland Stanford Junior University, Stanford, CA (US); The United States of America, as represented by the Secretary, Department of Health and Human Services, Bethesda, MD (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/550,881

(22) Filed: Dec. 14, 2021

(65) Prior Publication Data
US 2022/0098322 A1    Mar. 31, 2022

Related U.S. Application Data

(63) Continuation of application No. 16/902,068, filed on Jun. 15, 2020, now Pat. No. 11,230,607, which is a continuation of application No. 16/214,507, filed on Dec. 10, 2018, now Pat. No. 10,723,803, which is a continuation of application No. 15/676,296, filed on Aug. 14, 2017, now Pat. No. 10,184,004, which is a continuation of application No. 14/763,758, filed as application No. PCT/US2014/014905 on Feb. 5, 2014, now Pat. No. 9,771,428.

(60) Provisional application No. 61/761,133, filed on Feb. 5, 2013.

(51) Int. Cl.
*C07K 16/28* (2006.01)
*A61K 38/17* (2006.01)
*A61K 39/00* (2006.01)

(52) U.S. Cl.
CPC ...... *C07K 16/2896* (2013.01); *A61K 38/1774* (2013.01); *C07K 16/2803* (2013.01); *A61K 2039/505* (2013.01); *C07K 2317/24* (2013.01); *C07K 2317/76* (2013.01); *Y02A 50/30* (2018.01)

(58) Field of Classification Search
CPC .......... A61K 2039/505; A61K 38/1774; A61P 31/12; C07K 16/2803; C07K 16/2896; C07K 2317/24; C07K 2317/76; G11B 19/124
See application file for complete search history.

(56) References Cited

U.S. PATENT DOCUMENTS

| 8,728,476 B2 | 5/2014 | Van Den Berg |
| 9,771,428 B2 * | 9/2017 | Weiskopf ................ A61P 31/12 |
| 10,723,803 B2 * | 7/2020 | Weiskopf ........... C07K 16/2896 |

FOREIGN PATENT DOCUMENTS

| WO | WO1995/010265 | 4/1995 |
| WO | WO2009/131453 | 10/2009 |
| WO | WO2010/130053 | 11/2010 |
| WO | WO2011/143624 | 11/2011 |

OTHER PUBLICATIONS

Campadelli-Fiume et al., (2007) "The multipartite system that mediates entry of herpes simplex virus into the cell", Reviews in Mecial Virology, pp. 313-326, vol. 17, John Wiley & Sons, Inc., Hoboken, NJ.
Li et al., (2015) "The hepatitis B virus receptor", Annu. Rev. Cell Dev. Biol., pp. 125-147, vol. 31, Annual Reviews, Palo Alto, CA.
Mittal et al.,(2010) "*Escherichia coli* K1 promotes the ligation of CD47 with thrombospondin-1 to prevent the maturation of dendritic cells in the pathogenesis of neonatal meningitis", J. Immunology, pp. 2998-3006, vol. 185, Issue 5, The American Association of Immunologists, Inc., Rockville, MD.4.
Mortaz, (2015) "Role of pattern recognition receptors in Mycobacterium tuberculosis infection", International Journal of Mycobacteriology, p. 66, vol. 4, Supplement 1, Elsevier, Amsterdam, Netherlands.
Subbarayal et al., (2015) "EphrinA2 Receptor (EphA2) Is an Invasion and Intracellular Signaling Receptor for Chlamydia trachomatis", PLOS Pathg, pp. 1-32, PLOS, San Francisco, CA.
Suparak et al., (2011) "Burkholderia pseudomallei-induced cell fusion in U937 macrophages can be inhibited by monoclonal antibodies against host cell surface molecules", Microbes and Infection, pp. 1006-1011, vol. 13, No. 2, Elsevier, Amsterdam, Netherlands.

(Continued)

*Primary Examiner* — Bao Q Li
(74) *Attorney, Agent, or Firm* — Pamela J. Sherwood; Bozicevic, Field & Francis LLP

(57) ABSTRACT

Methods are provided for treating a subject with for an intracellular pathogen infection, by administering an agent that reduces the binding of CD47 on a infected cell to SIRPα on a host phagocytic cell, in an effective dose for increasing the phagocytosis of infected cells.

28 Claims, 14 Drawing Sheets
Specification includes a Sequence Listing.

(56) References Cited

OTHER PUBLICATIONS

Willingham et al.,(2012) "The CD47-Signal Regulatory Protein Alpha (SIRP-alpha) Interaction Is A Therapeutic Target For Human Solid Tumors", PNAS, pp. 6662-6667, vol. 109, No. 17, PNAS, Washington, DC.

* cited by examiner

Fig. 2B Representative Histogram

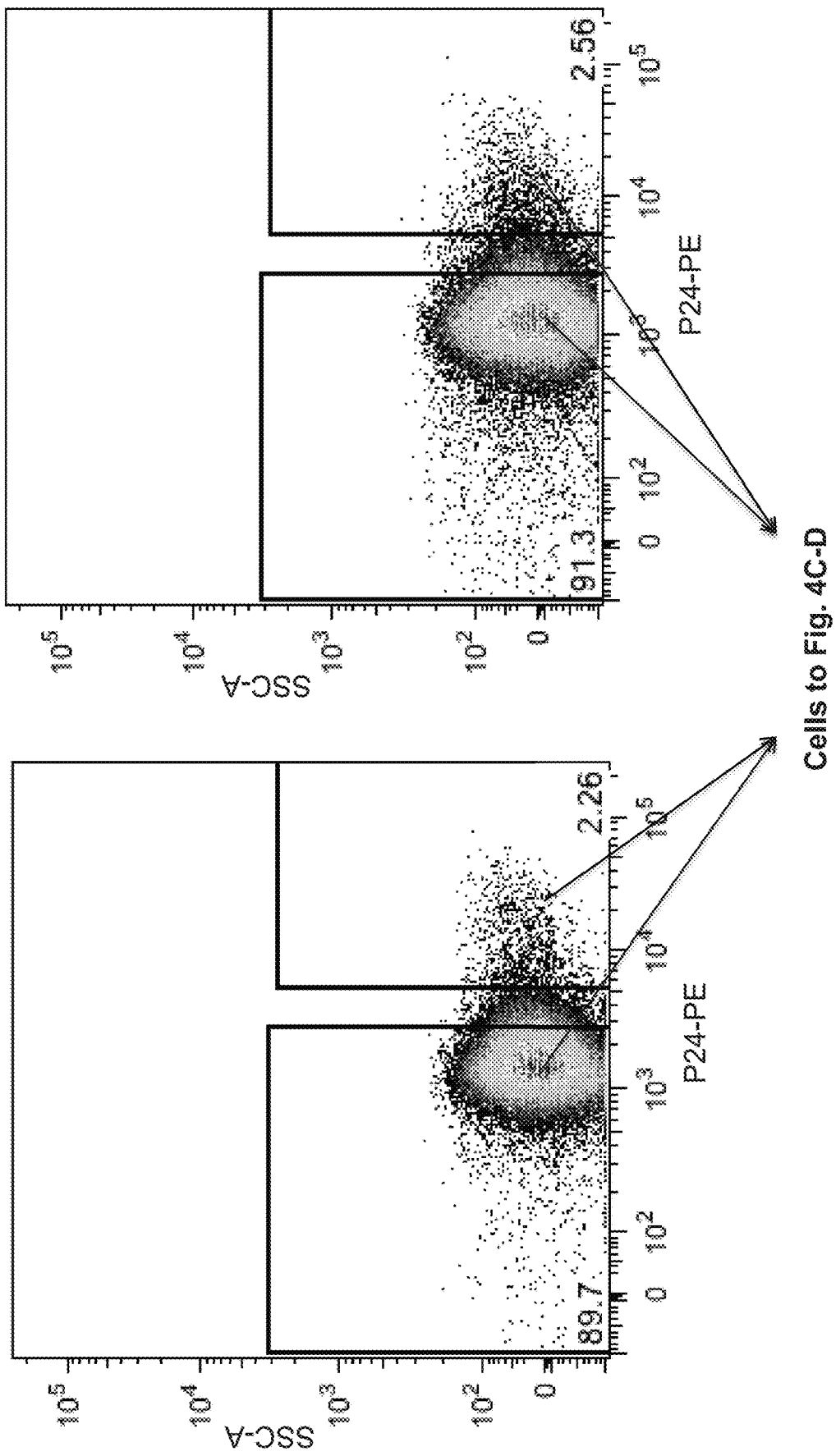

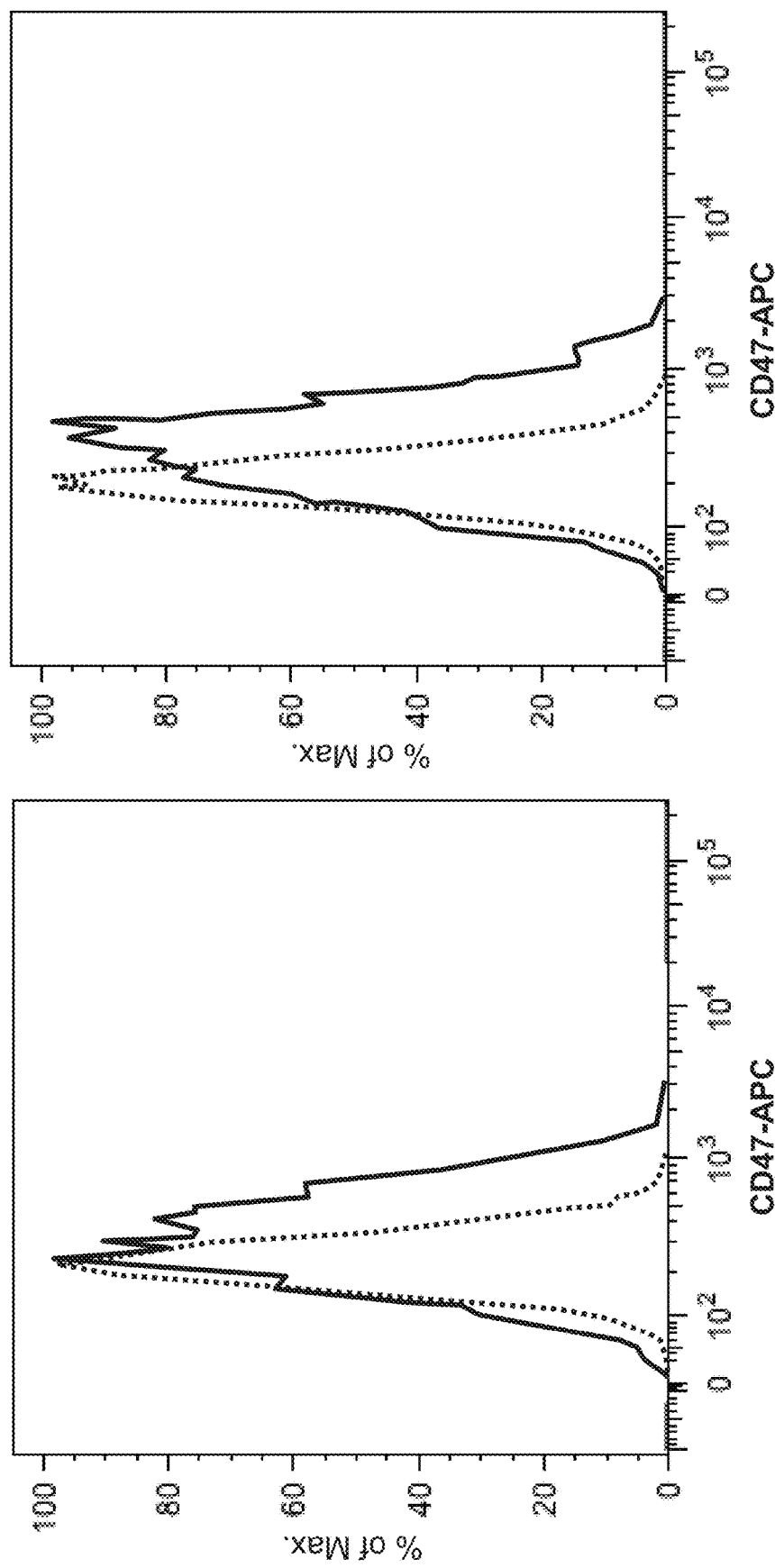

Fig. 7A

| Implantation date | 12/29/11 |
| --- | --- |
| Implant age | 26 weeks |
| Donor ID | #122811 |
| Inoculation date | 6/28/12 |
| Virus | HIV-1 YK-JRCSF; batch 11/16/07 (undiluted) |
| Inoculum | 1,800 TCID$_{50}$ per implant |
| Termination date | 8/9/12 (42 days after inoculation) 8/30/12 (63 days after inoculation, 3 weeks after treatment initiation) |
| Drug | anti-CD47 (Stanford, #SF9-hIgG4, 1.5 mg/ml, lot #6-18-12) control Ab (Stanford, #control h-IgG, 1.5 mg/ml, lot #6-18-12) |
| Route | intraperitoneal |
| Dosing | 300 μg three times per week (Monday, Wednesday, Friday) |
| Volume | 200 μl |
| Treatment initiation | 43 days after virus inoculation |

Fig. 7B

| Group | Mice/group | Virus | Drug | Dose (µg) | Implant collection (weeks after inoculation) | p24 (pg/10⁶ cells) | p24 (% of control) | HIV-1 RNA ($\log_{10}$ copies/ $10^6$ cells) |
|---|---|---|---|---|---|---|---|---|
| A | 3 | JR-CSF | — | — | 6 | 81 ± 1.9 | 51 ± 1.2 | 4.2 ± 0.07 |
| B/C† | 7 | JR-CSF | anti-CD47 | 300 | 9 | 47 ± 6.3* | 29 ± 3.9 | 4.4 ± 0.17 |
| D/E† | 6 | JR-CSF | control Ab | 300 | 9 | 96 ± 14** | 60 ± 8.9 | 4.5 ± 0.16 |
| F/G | 6 | JR-CSF | — | — | 9 | 160 ± 43 | 100 ± 27 | 4.8 ± 0.16 |
| H | 3 | medium | — | — | 6 | negative | 0.0 ± 0.0 | negative |
| I/J | 6 | medium | — | — | 9 | negative | 0.0 ± 0.0 | negative |

\* $P \leq 0.050$ anti-CD47 treated JR-CSF-infected mice (group B/C) compared to untreated JR-CSF-infected mice (group F/G) by Mann-Whitney U test.

\*\* $P \leq 0.050$ control Ab treated JR-CSF-infected mice (group D/E) compared to anti-CD47 treated JR-CSF-infected mice (groups B/C) by Mann-Whitney U test.

†group B: mouse #8 excluded from analyses (whole body lymphoma).

†group D: mouse #15 implant excluded from analyses (abnormal cell profile).

Fig. 7C

| Group | Mice/group | Virus | Drug | FACS analysis ||||||
|---|---|---|---|---|---|---|---|---|---|
| | | | | Gag-p24+ thymocytes (%) | CD4+CD8+ (%) | CD4+ (%) | CD8+ (%) | CD4/CD8 ratio | W6/32 mean fluorescence intensity | Live thymocytes (%) |
| A | 3 | JR-CSF | — | 0.77 ± 0.12 | 80 ± 2.6 | 6.9 ± 1.2 | 3.4 ± 0.56 | 2.0 ± 0.07 | 7700 ± 580 | 70 ± 2.0 |
| B/C† | 7 | JR-CSF | anti-CD47 | 0.54 ± 0.06 | 70 ± 7.5 | 18 ± 5.3 | 6.8 ± 1.8 | 2.6 ± 0.13* | 2800 ± 190 | 44 ± 5.2 |
| D/E† | 6 | JR-CSF | control Ab | 0.81 ± 0.19 | 84 ± 1.7** | 7.7 ± 0.39** | 4.1 ± 0.41 | 1.9 ± 0.11** | 3100 ± 130 | 47 ± 3.6 |
| F/G | 6 | JR-CSF | — | 0.62 ± 0.05 | 76 ± 4.6 | 9.3 ± 1.4 | 4.9 ± 0.53 | 1.8 ± 0.13 | 3000 ± 190 | 49 ± 2.8 |
| H | 3 | medium | — | 0.45 ± 0.06 | 77 ± 2.5 | 8.1 ± 1.6 | 3.9 ± 1.3 | 2.3 ± 0.41 | 2700 ± 430 | 77 ± 1.8 |
| I/J | 6 | medium | — | 0.34 ± 0.11 | 78 ± 6.3 | 13 ± 4.4 | 4.3 ± 1.0 | 2.7 ± 0.20 | 2000 ± 64 | 45 ± 6.8 |

* $P \leq 0.050$ anti-CD47 treated JR-CSF-infected mice (group B/C) compared to untreated JR-CSF-infected mice (group F/G) by Mann-Whitney U test.

** $P \leq 0.050$ control Ab treated JR-CSF-infected mice (group D/E) compared to anti-CD47 treated JR-CSF-infected mice (groups B/C) by Mann-Whitney U test.

†group B: mouse #8 excluded from analyses (whole body lymphoma).

†group D: mouse #15 implant excluded from analyses (abnormal cell profile).

Fig. 7D

| Group | Mice/group | Virus | Drug | Total cell yield ($10^6$) | Live thymocyte yield ($10^6$) | Body weight change (%) |
|---|---|---|---|---|---|---|
| A | 3 | JR-CSF | — | 310 ± 60 | 210 ± 38 | N/A |
| B/C† | 7 | JR-CSF | anti-CD47 | 110 ± 64 | 57 ± 36 | −3.0 |
| D/E† | 6 | JR-CSF | control Ab | 140 ± 32 | 63 ± 13 | −2.2 |
| F/G | 6 | JR-CSF | — | 240 ± 72 | 120 ± 40 | −3.2 |
| H | 3 | medium | — | 490 ± 72 | 370 ± 47 | N/A |
| I/J | 6 | medium | — | 190 ± 49 | 99 ± 29 | −4.5 |

†group B: mouse #8 excluded from analyses (whole body lymphoma).

†group D: mouse #15 implant excluded from analyses (abnormal cell profile).

CD47 TARGETED THERAPIES FOR THE TREATMENT OF INFECTIOUS DISEASE

CROSS REFERENCE

This application claims benefit and is a Continuation of application Ser. No. 16/902,068, filed Jun. 15, 2020, which is a Continuation of application Ser. No. 16/214,507, filed Dec. 10, 2018, now U.S. Pat. No. 10,723,803, issued Jul. 28, 2020, which is a Continuation of application Ser. No. 15/676,296, filed Aug. 14, 2017, now U.S. Pat. No. 10,184, 004, issued Jan. 22, 2019, which is a Continuation of application Ser. No. 14/763,758, filed Jul. 27, 2015, now U.S. Pat. No. 9,771,428, issued Sep. 26, 2017, which is a 371 application and claims the benefit of PCT Application No. PCT/US2014/014905, filed Feb. 5, 2014, which claims benefit of U.S. Provisional Patent Application No. 61/761, 133, filed Feb. 5, 2013, which applications are incorporated herein by reference in their entirety.

FEDERALLY SPONSORED RESEARCH AND DEVELOPMENT

This invention was made with Government support under contracts CA168059, GM007365, and HHSN266200700002C awarded by the National Institutes of Health. The Government has certain rights in the invention.

BACKGROUND OF THE INVENTION

Turnover of cells begins with the induction of an apoptotic program or other cellular changes that mark them for removal, and the subsequent recognition of markers by phagocytes, including macrophages, dendritic cells, and the like. This process requires a specific and selective removal of unwanted cells. Unlike healthy cells, the unwanted/aged/dying cells display markers or ligands called "eat-me" signals, i.e. "altered self", which can in turn be recognized by receptors on the phagocytes. Healthy cells may display "don't eat-me" signals that actively inhibit phagocytosis; these signals are either downregulated in the dying cells, are present in an altered conformation or they are superseded by the upregulation of "eat-me" or pro-phagocytic signals. The cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte, or the loss of CD47 expression in knockout mice, can cause removal of live cells and non-aged erythrocytes. Alternatively, blocking SIRPα also allows engulfment of targets that are not normally phagocytosed, for those cells where pre-phagocytic signals are also present.

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2007) J.B.C. 282:14567-75; and the role of SIRPα cis dimerization in CD47 binding is discussed by Lee et al. (2010) J.B.C. 285:37953-63.

In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo. CD47 is also constitutively upregulated on a number of cancers. Overexpression of CD47 by tumor cells may increase pathogenicity by allowing the cell to evade phagocytosis.

Programmed cell death (PCD) and phagocytic cell removal are common ways that damaged, precancerous, inflamed, or infected cells respond to pathogenic threats to the organism. However, some infections persist for long periods of time, suggesting that successful persistent infections overcome the PCD and phagocytic cell removal pathways. The identification and targeting of a mechanism by which infectious agents overcome PCD and/or phagocytic cell removal will prove useful for the treatment of infectious disease via disruption of the identified mechanism. The present invention provides methods for treatment of infectious disease using CD47 blocking reagents.

SUMMARY OF THE INVENTION

Methods are provided for treating an individual infected with an intracellular pathogen, by administering an effective dose of an agent that reduces the binding between CD47 present on a cell infected with the intracellular pathogen, to SIRPα on a phagocytic cell present in the individual, where the dose is effective in increasing the phagocytosis of infected cells. Suitable agents include soluble high affinity SIRPα polypeptides; soluble CD47; anti-CD47 antibodies, anti-SIRPα antibodies, and the like. Antibodies of interest include humanized antibodies, or caninized, felinized, equinized, bovinized, porcinized, etc., antibodies, and variants thereof.

Embodiments of the invention include treating a mammalian subject, including without limitation dog, cat, pig, sheep, cow, horse, human, etc. Embodiments of the invention include treating a subject for any intracellular pathogen infection. In particular embodiments the methods are used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehrlichia, Rickettsia, Brucella, Legionella, Francisella, Listeria, Coxiella, Neisseria, Salmonella, Yersinia* sp, etc.; and intracellular protozoan pathogens, e.g. *Plasmodium* sp., *Trypanosoma* sp., *Giardia* sp., *Toxoplasma* sp., *Leishmania* sp., etc.

In some embodiments, the methods provided are for targeting or depleting infected cells, comprising contacting a population of cells, e.g. blood from an infected subject, with an agent that specifically binds to CD47, in order to target or deplete infected cells. In certain aspects, the agent is an anti-CD47 antibody or high affinity soluble SIRPα conjugated to a cytotoxic agent, e.g., radioactive isotope, chemotherapeutic agent, toxin, etc. In some embodiments, the depletion is performed on an ex vivo population of cells (e.g., the purging of infected cells from the subject's blood). In another embodiment, methods are provided for in vivo targeting of infected cells in a subject by administering such an agent to the subject.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A and FIG. 1B) CD19+ B cells (FIG. 1C and FIG. 1D) Ter119+ Erythroid cells. "34+" is a marker of virus-infected cells while "34−" indicates uninfected cells.

FIG. 2A-2B demonstrates an upregulation of CD47 in Fr98-infected vs uninfected cells from the same animal (mouse neonates). "34+" is a marker of virus-infected cells while "34−" indicates uninfected cells. Fr98 is a neurotropic mouse leukemia virus.

(FIG. 3A) indicates the percent of each cell type that stained positive for mAb34+ when infected with virus compared to a mock infection. (FIG. 3B) indicates the level of CD47 expression per cell (MFI—Mean Fluorescence Intensity) for infected versus uninfected cells from the same animal. Multiple different cell types were assayed.

FIG. 4A-4D demonstrates an increase of CD47 expression upon HIV infection of human cells. (FIG. 4A-4B) T cells were isolated from people and either (FIG. 4A) HIV infected or (FIG. 4B) mock infected. The percent of cells expressing p24 antigen was determined by FACS. (FIG. 4C-4D) demonstrate increased CD47 expression on HIV-infected T cells relative to uninfected T cells within a single sample. The two graphs in FIG. 4C represent duplicate experiments. The two graphs in FIG. 4D represent duplicate experiments.

FIG. 7A-7D presents an evaluation of the antiviral activity of anti-CD47 humanized monoclonal antibody 5F9-hIgG4 against established HIV-1 (JR-CSF) infection in SCID-hu Thy/Liv mice treated by intraperitoneal injection. (FIG. 7A) summary of experimental protocol. (FIG. 7B) indicates HIV p24 antigen levels and HIV-1 RNA copy number following control or anti-CD47 treatment as indicated. (FIG. 7C) depicts flow cytometric analysis of human thymocytes following control or anti-CD47 treatment as indicated. (FIG. 7D) shows absolute cell counts and body weight change from treated animals.

DETAILED DESCRIPTION OF THE INVENTION

Figure 1A:
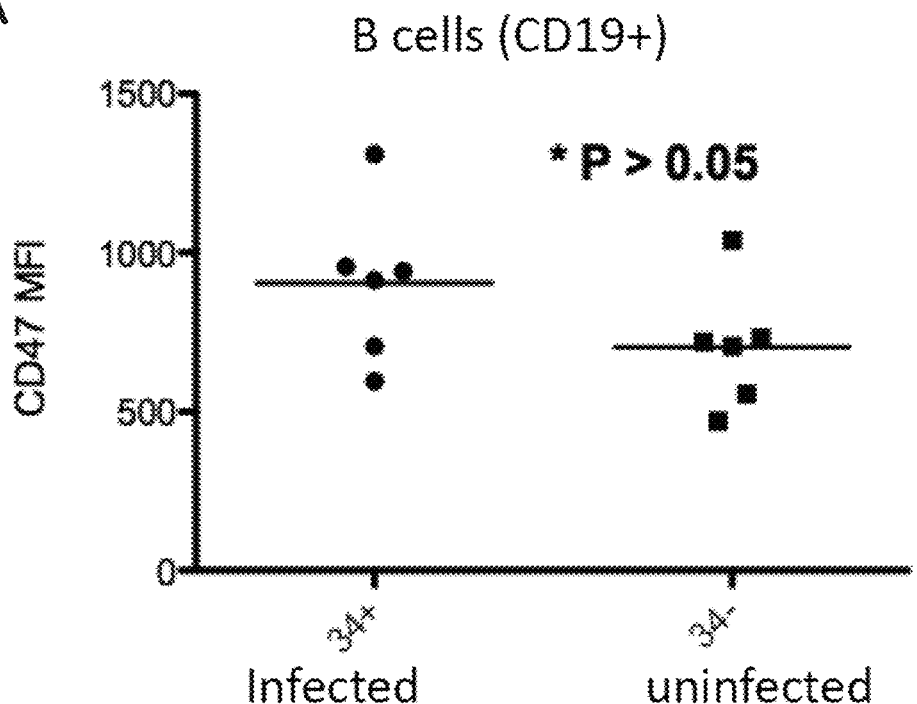
FIG. 1A-1D demonstrates an upregulation of CD47 in Friend Virus (FV)-infected cells compared to uninfected cells from the same animal (7 days post-infection of adult mice).
Figure 1B:
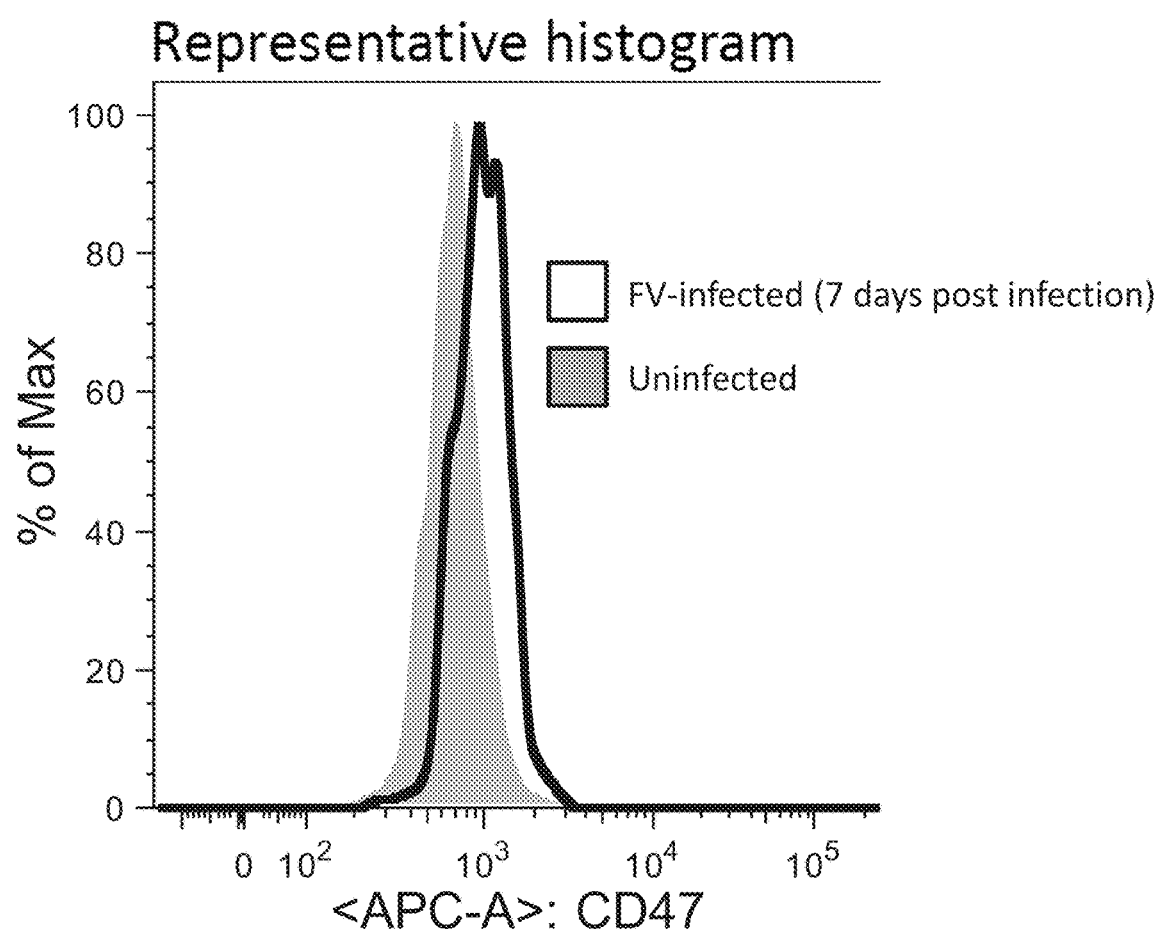
Figure 1C:
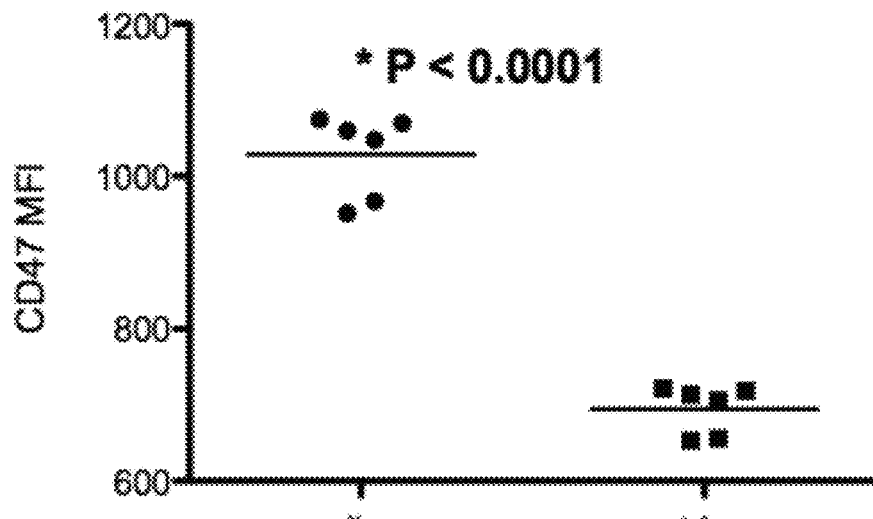
Figure 1D:
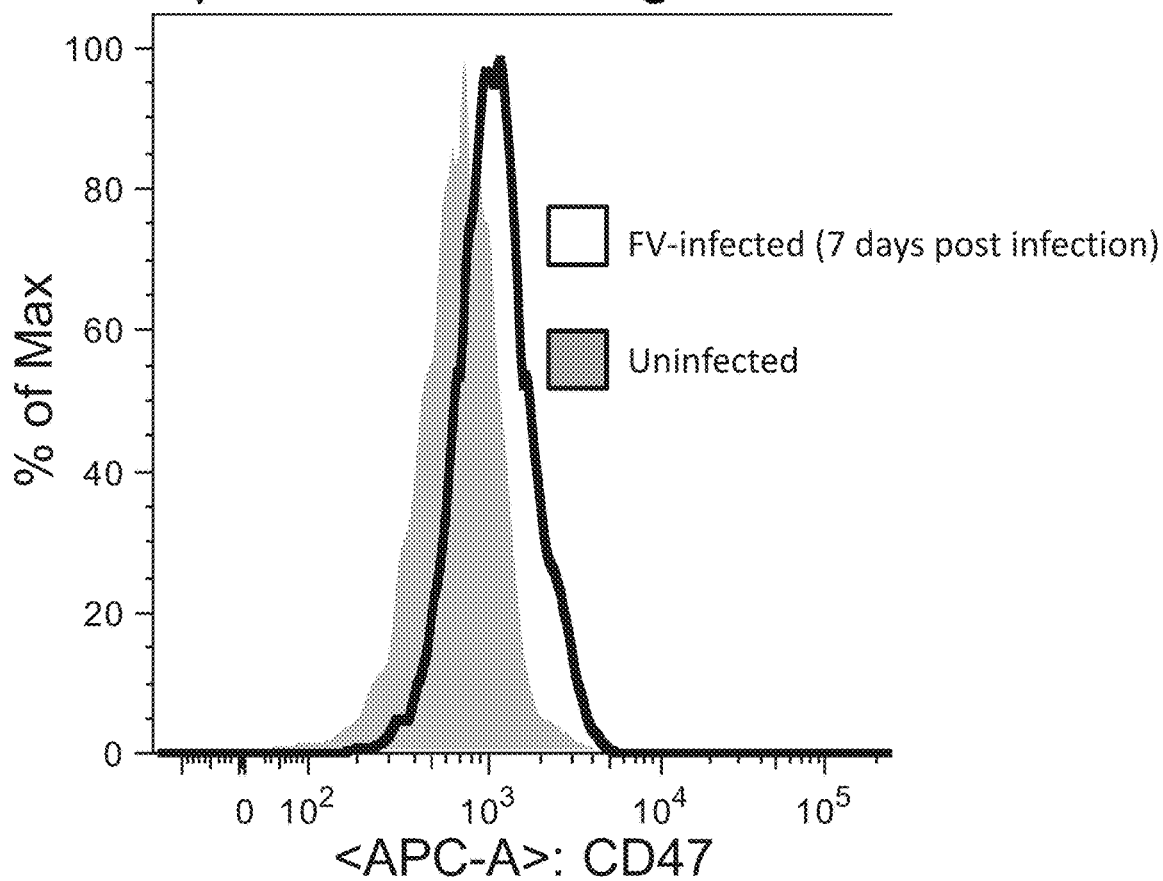

The present invention relates to methods of treating a subject for an infection by administering an agent that reduces the binding of CD47 to SIRPα, which may be referred to herein as an anti-CD47 agent.

The terms "treatment", "treating", "treat" and the like are used herein to generally refer to obtaining a desired pharmacologic and/or physiologic effect. The effect can be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom. Those in need of treatment include those already with an infection as well as those in which an infection is to be prevented. As such, a therapeutic treatment is one in which the subject is infected prior to administration and a prophylactic treatment is one in which the subject is not infected prior to administration. In some embodiments, the subject is suspected of being infected prior to administration. In some embodiments, the subject has an increased risk of infection prior to administration. In some embodiments, the subject is suspected of being at increased risk of infection prior to administration.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

An "effective amount" is an amount sufficient to effect beneficial or desired clinical results. An effective amount can be administered in one or more administrations. For purposes of this invention, an effective amount of an anti-CD47 agent is an amount that is sufficient to palliate, ameliorate, stabilize, reverse, prevent, slow or delay the progression of the disease state (e.g., infection) by increasing phagocytosis of a target cell.

As used herein, a "target cell" is a cell expressing CD47 on the surface, where masking or otherwise altering the CD47 positive phenotype (e.g., by administration of an anti-CD47 agent) results in increased phagocytosis. Usually a target cell is a mammalian cell, for example a human cell.

As used herein, the term "infection" refers to any state in at least one cell of an organism (i.e., a subject) is infected by an infectious agent. As used herein, the term "infectious agent" refers to a foreign biological entity, i.e. a pathogen, that induces increased CD47 expression in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions.

As used herein, the term "anti-CD47 agent" refers to any agent that reduces the binding of CD47 (e.g., on an infected cell) to SIRPα (e.g., on a phagocytic cell). Non-limiting examples of suitable anti-CD47 reagents include high affinity SIRPα reagents, anti-SIRPα antibodies, soluble CD47 polypeptides, and anti-CD47 antibodies or antibody fragments. In some embodiments, a suitable anti-CD47 agent (e.g. an anti-CD47 antibody, a high affinity SIRPα reagent, etc.) specifically binds CD47 to reduce the binding of CD47 to SIRPα. In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent (further described below). In an exemplary assay, infected cells are incubated in the presence or absence of the candidate agent. An agent for use in the methods of the invention will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 160%, or at least 200%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) occurs (Manna and Frazier, Cancer Research, 64, 1026-1036, Feb. 1, 2004). Thus, in some embodiments, the anti-CD47 agent does not directly induce cell death of a CD47-expressing cell.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides, or high affinity binding of a SIRPα polypeptide). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Suitable specific binding members include agents that specifically bind CD47 (i.e., anti-CD47 agents), or that otherwise block the interaction between CD47 and SIRPα.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

In one embodiment of the invention, the anti-CD47 agent, or a pharmaceutical composition comprising the agent, is provided in an amount effective to detectably inhibit the binding of CD47 to SIRPα present on the surface of phagocytic cells. The effective amount is determined via empirical testing routine in the art, for example in a biological sample taken from an infected individual. The effective amount may vary depending on the number of cells being targeted, the location of the cells, and factors specific to the subject.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's infected cell, e.g., a sample comprising polynucleotides and/or polypeptides that is obtained from a patient's infected cell (e.g., a cell lysate or other cell extract comprising polynucleotides and/or polypeptides); and a sample comprising infected cells from a patient. A biological sample comprising an infected cell from a patient can also include non-infected cells.

High affinity SIRPα reagent. In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. In other embodiments, the second polypeptide is any suitable polypeptide that is substantially similar to Fc, e.g., providing increased size, multimerization domains, and/or additional binding or interaction with Ig molecules.

A suitable high affinity SIRPα reagent reduces (e.g., blocks, prevents, etc.) the interaction between the native proteins SIRPα and CD47. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference).

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of infected cells over non-infected cells. Those cells that express higher levels of CD47 (e.g., infected cells) relative to other cells (non-infected cells) will be preferentially phagocytosed. Thus, a suitable anti-SIRPα antibody specifically binds SIRPα without activating/stimulating enough of a signaling response to inhibit phagocytosis.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to other cells (non-infected cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide (SEQ ID NO:2), such that the extracellular portion of CD47 is typically 142 amino acids in length, and has the amino acid sequence set forth in SEQ ID NO:3. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. In an exemplary embodiment, the CD47 extracellular domain lacking the signal peptide has the amino acid sequence set forth in SEQ ID NO:1 (124 amino acids). As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to SEQ ID NO:1.

In some cases, an anti-CD47 agent is not a soluble CD47 polypeptide (i.e., is an anti-CD47 agent other than a soluble CD47 polypeptide). In some cases, an anti-CD47 agent binds to SIRPα but is not a soluble CD47 polypeptide (i.e., is a SIRPα binding anti-CD47 agent other than a soluble CD47 polypeptide).

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Suitable anti-CD47 antibodies include fully human, humanized or chimeric versions of such antibodies. Humanized antibodies are especially useful for in vivo applications in humans due to their low antigenicity. Similarly caninized, felinized, etc antibodies are especially useful for applications in dogs, cats, and other species respectively.

Methods

Methods are provided for treating or reducing infection, including without limitation bacterial, viral, protozoan, and fungal infections, by inhibiting the interaction between SIRPα and CD47, thereby increasing in vivo phagocytosis of infected cells. Such methods include administering to a subject in need of treatment a therapeutically effective amount or an effective dose of an anti-CD47 agent, including without limitation combinations of the reagent with another drug.

In some embodiments the infection is a chronic infection, i.e. an infection that is not cleared by the host immune system within a period of up to 1 week, 2 weeks, etc. In some cases, chronic infections involve integration of pathogen genetic elements into the host genome, e.g. retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses.

Viral pathogens of interest include without limitation, retroviral and lentiviral pathogens, e.g. HIV-1; HIV-2, HTLV, FIV, SIV, etc., Hepatitis B virus, etc. Microbes of interest include, but not limited to the following, include: *Yersinia* sp., e.g. *Y. pestis, Y. pseudotuberculosis, Y enterocolitica; Francisella* sp.; *Pasteurella* sp.; *Vibrio* sp., e.g. *V. cholerae, V. parahemolyticus; Legionella* sp., e.g. *L. pneumophila;* *Listeria* sp., e.g. *L. monocytogenes; Mycoplasma* sp., e.g. *M. hominis, M. pneumoniae; Mycobacterium* sp., e.g. *M. tuberculosis, M. leprae; Rickettsia* sp., e.g. *R. rickettsii, R. typhi; Chlamydia* sp., e.g. *C. trachomatis, C. pneumoniae, C. psittaci; Helicobacter* sp., e.g. *H. pylori*, etc. Also included are intracellular protozoan pathogens, e.g. *Plasmodium* sp, *Trypanosoma* sp., *Giardia* sp., *Toxoplasma* sp., *Leishmania* sp., etc. In some cases, the pathogen is not a virus. In some cases, the pathogen is not a pox virus. In some cases, the pathogen is a virus, but is not a pox virus (i.e., the pathogen is a virus other than a pox virus). In some cases, the pathogen is a virus, but is not a vaccinia virus (i.e., the pathogen is a virus other than a vaccinia virus). In some cases, the pathogen is a virus, but is not a molluscum contagiosum virus (MCV) (i.e., the pathogen is a virus other than MCV). In some cases, the pathogen is a virus, but is not a pox virus, a vaccinia virus, or a molluscum contagiosum virus (MCV) (i.e., the pathogen is a virus other than a pox virus, vaccinia virus, or MCV).

An infection treated with the methods of the invention generally involves a pathogen with at least a portion of its life-cycle within a host cell, i.e. an intracellular phase. The methods of the invention provide for a more effective removal of infected cells by the phagocytic cells of the host organism, relative to phagocytosis in the absence of treatment, and thus are directed to the intracellular phase of the pathogen life cycle.

In some embodiments, the methods of the invention involve diagnosis of a patient as suffering from a pathogenic intracellular infection; or selection of a patient previously diagnosed as suffering from a pathogenic intracellular infection; treating the patient with a regimen of anti-CD47 therapy, optionally in combination with an additional therapy; and monitoring the patient for efficacy of treatment. Monitoring may measure clinical indicia of infection, e.g. fever, white blood cell count, etc., and/or direct monitoring for presence of the pathogen.

Treatment may be combined with other active agents. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenicol; metronidazole; spectinomycin; trimethoprim; vancomycin; etc. Cytokines may also be included, e.g. interferon γ, tumor necrosis factor α, interleukin 12, etc. Antiviral agents, e.g. acyclovir, gancyclovir, etc., may also be used in treatment.

Effective doses of the therapeutic entity of the present invention vary depending upon many different factors, including the nature of the anti-CD47 agent, means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage can range from about 0.0001 to 500 mg/kg, and more usually 0.01 to 100 mg/kg, of the host body weight. For example dosages can be 1 mg/kg body weight or 10 mg/kg body weight or within the range of 1-50 mg/kg. The dosage may be adjusted for the molecular weight of the reagent. An exemplary treatment regime entails administration daily, semi-weekly, weekly, once every two weeks, once a month, etc. In another example, treatment can be given as a continuous infusion. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient. It will be understood by one of skill in the art that such guidelines will be adjusted for the molecular weight of the active agent, e.g. in the use of antibody fragments, in the use of antibody conjugates, in the use of high affinity SIRPα reagents, etc. The dosage may also be varied for localized administration, e.g. intranasal, inhalation, etc., or for systemic administration, e.g. i.m., i.p., i.v., and the like.

For the treatment of disease, the appropriate dosage of the anti-CD47 agent will depend on the type of disease to be treated, as defined above, the severity and course of the disease, whether the agent is administered for preventive purposes, previous therapy, the patient's clinical history and response to the antibody, and the discretion of the attending physician. The anti-CD47 agent is suitably administered to the patient at one time or over a series of treatments.

Suitable anti-CD47 agents can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of an anti-CD47 agent includes use in combination with another therapeutic agent, e.g., another anti-infection agent. Therapeutic formulations comprising one or more anti-CD47 agents of the invention are prepared for storage by mixing the anti-CD47 agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The anti-CD47 agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the anti-CD47 agent to be administered will be governed by such considerations, and is the minimum amount necessary to prevent the CD47 associated disease.

The anti-CD47 agent can be administered by any suitable means, including topical, oral, parenteral, subcutaneous, intraperitoneal, intrapulmonary, and intranasal. Parenteral infusions include intramuscular, intravenous, intraarterial, intraperitoneal, intrathecal or subcutaneous administration. In addition, the anti-CD47 agent is suitably administered by pulse infusion, particularly with declining doses of the agent.

The anti-CD47 agent need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

An anti-CD47 agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an anti-CD47 agent by non-covalent associations, such as non-covalent bonding or by encapsulation. The nature of the carrier can be either soluble or insoluble for purposes of the invention. Those skilled in the art will know of other suitable carriers for binding anti-CD47 agents, or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethyl-benzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules)

or in macroemulsions. Such techniques are disclosed in Remington's Pharmaceutical Sciences 16th edition, Osol, A. Ed. (1980).

Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the methods of the invention. Such moieties may be conjugated to the anti-CD47 agent through an acceptable chemical linker or chelation carrier. Positron emitting moieties for use in the present invention include $^{18}F$, which can be easily conjugated by a fluorination reaction with the anti-CD47 agent.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249:1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the anti-CD47 agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

The data presented here demonstrate that increased expression of CD47 is a common mechanism by which infectious agents (e.g., viruses, fungi, bacteria, protozoa, etc.) circumvent the immune response of the host organism. When an infected cell is induced by an infectious agent to express increased levels of CD47, the infected cell presents a "don't eat me" signal (CD47) to the host organism's macrophages and phagocytes. Thus, the infectious agent prevents the phagocytosis and removal of the infected cell. To counteract this process and allow the phagocytosis and removal of infected cells in a subject, an anti-CD47 agent can be administered to reduce the binding of CD47 on the infected cell, to SIRPα on a phagocytic host cell and thus allowing the eat me signals to prevail.

The following experiments were performed, revealing that cells infected with various infectious agents express higher levels of CD47 than uninfected cells.

Adult mice were experimentally infected with the Friend Virus (FV virus, a strain of murine leukemia virus that is a member of retroviridae having a ssRNA genome). Uninfected and infected cells (i.e., FV-infected cells) from the same animal were isolated 7 days post-infection and assayed via Fluorescent activated cell sorting (FACS) to determine relative expression levels of CD47 (using an anti-CD47 antibody). FV-infected cells (B cells as well as Erythroid cells) expressed higher levels of CD47 compared to uninfected cells from the same animal (FIG. 1A-1D).

Figure 2A:
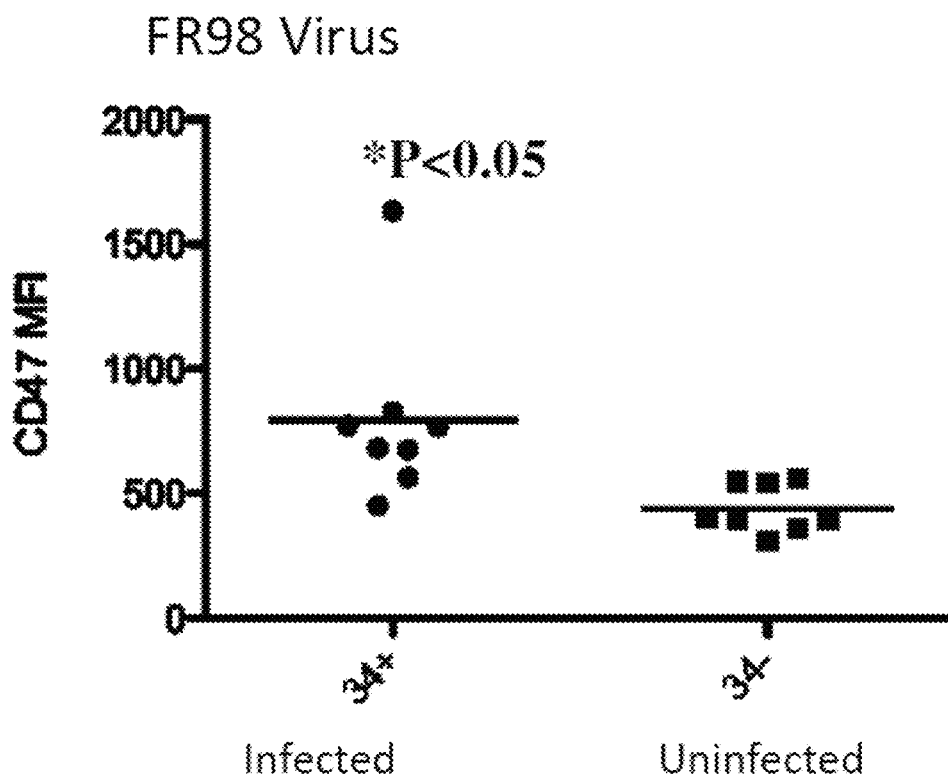
Figure 2A:
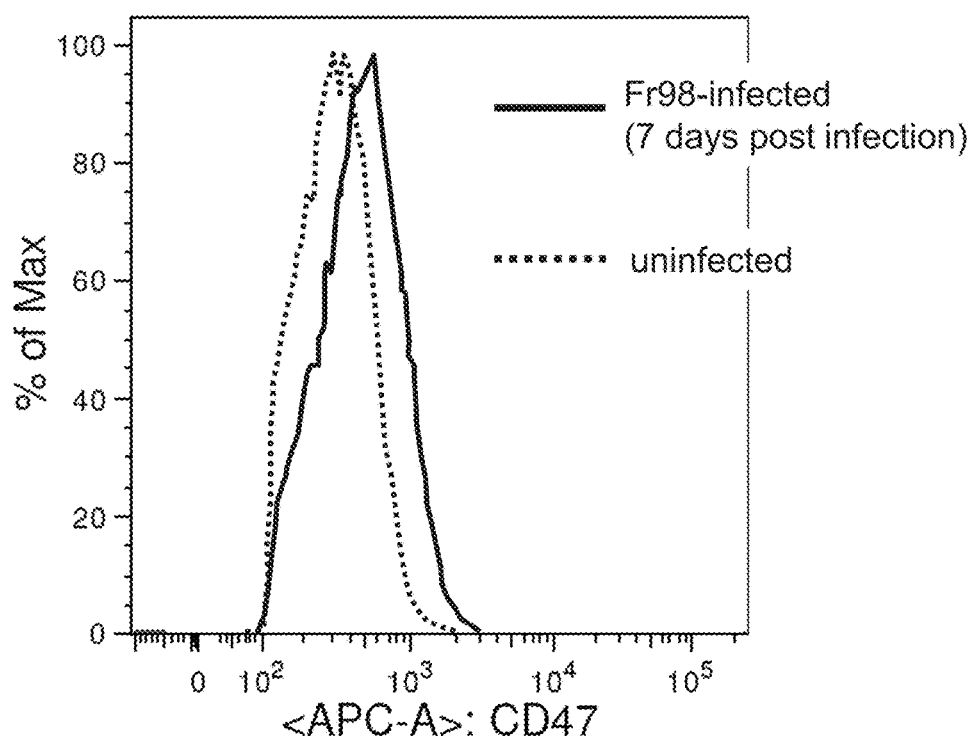
Figure 3A:
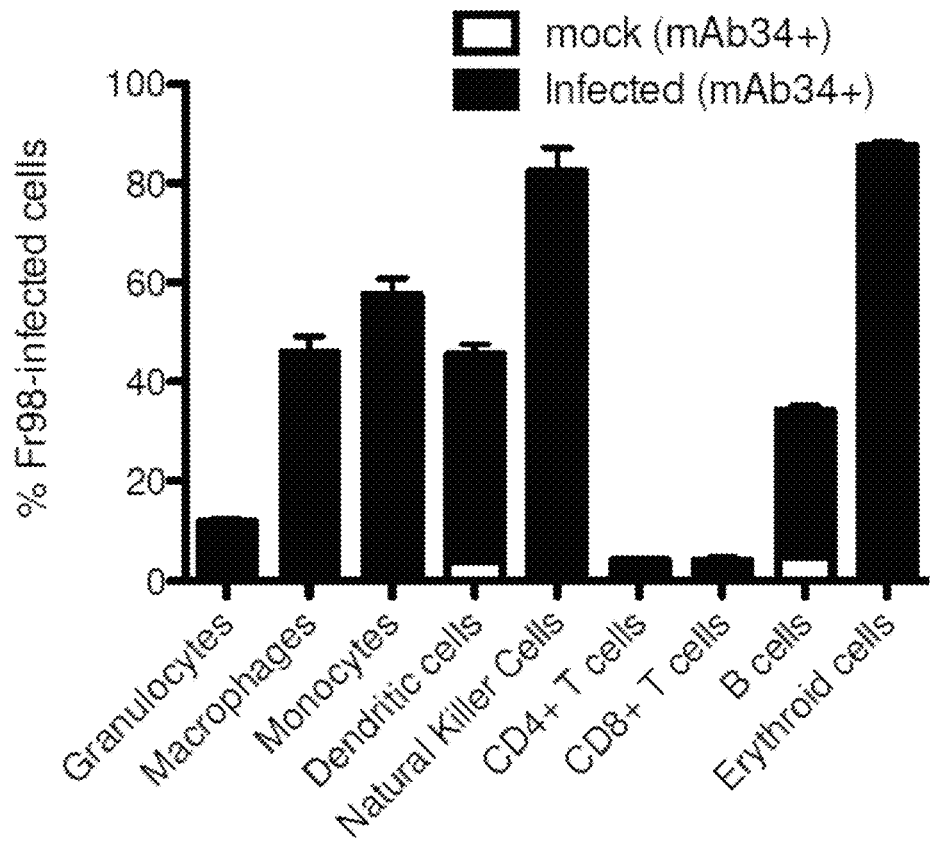
FIG. 3A-3B demonstrates an upregulation of CD47 in individual cell types that are infected with the Fr98 neurotropic mouse leukemia virus.
Figure 3B:
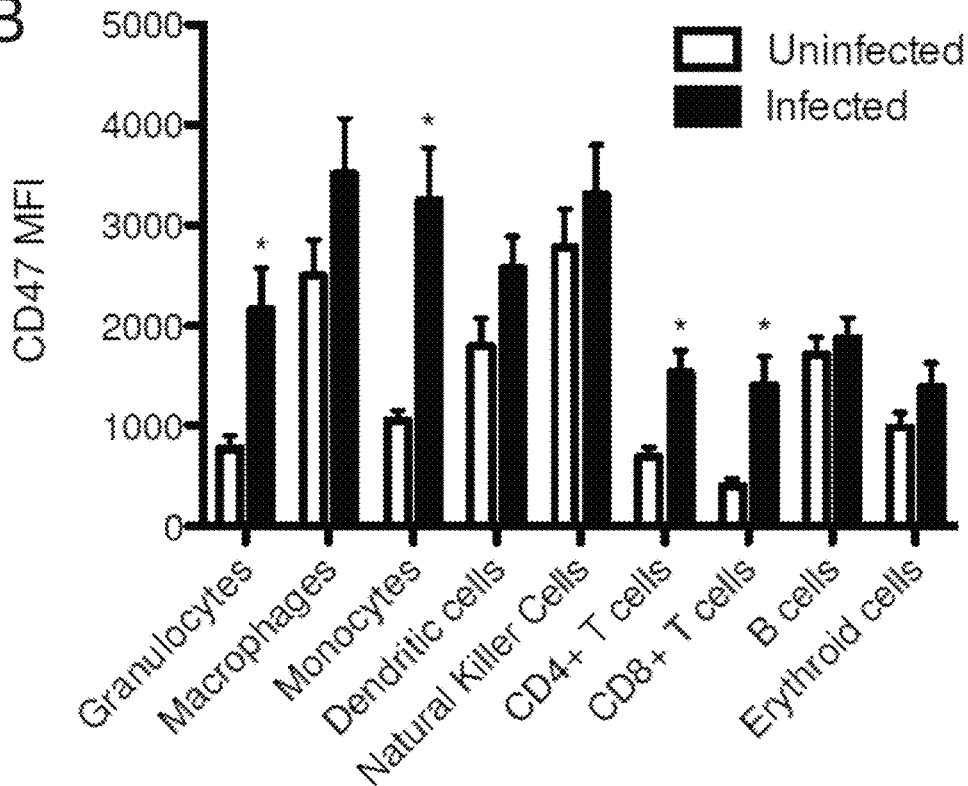
Figure 4B:
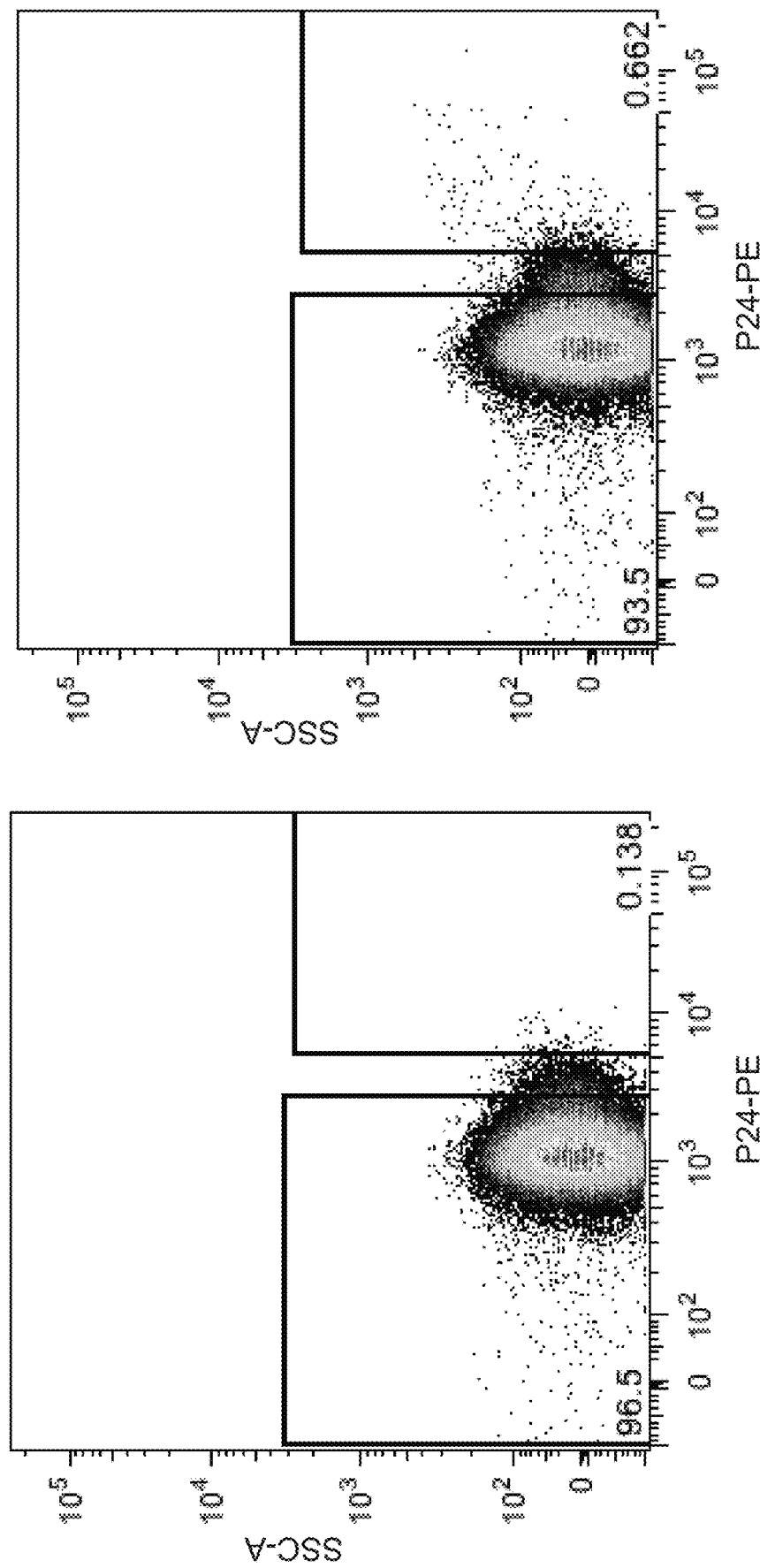
Figure 4D:
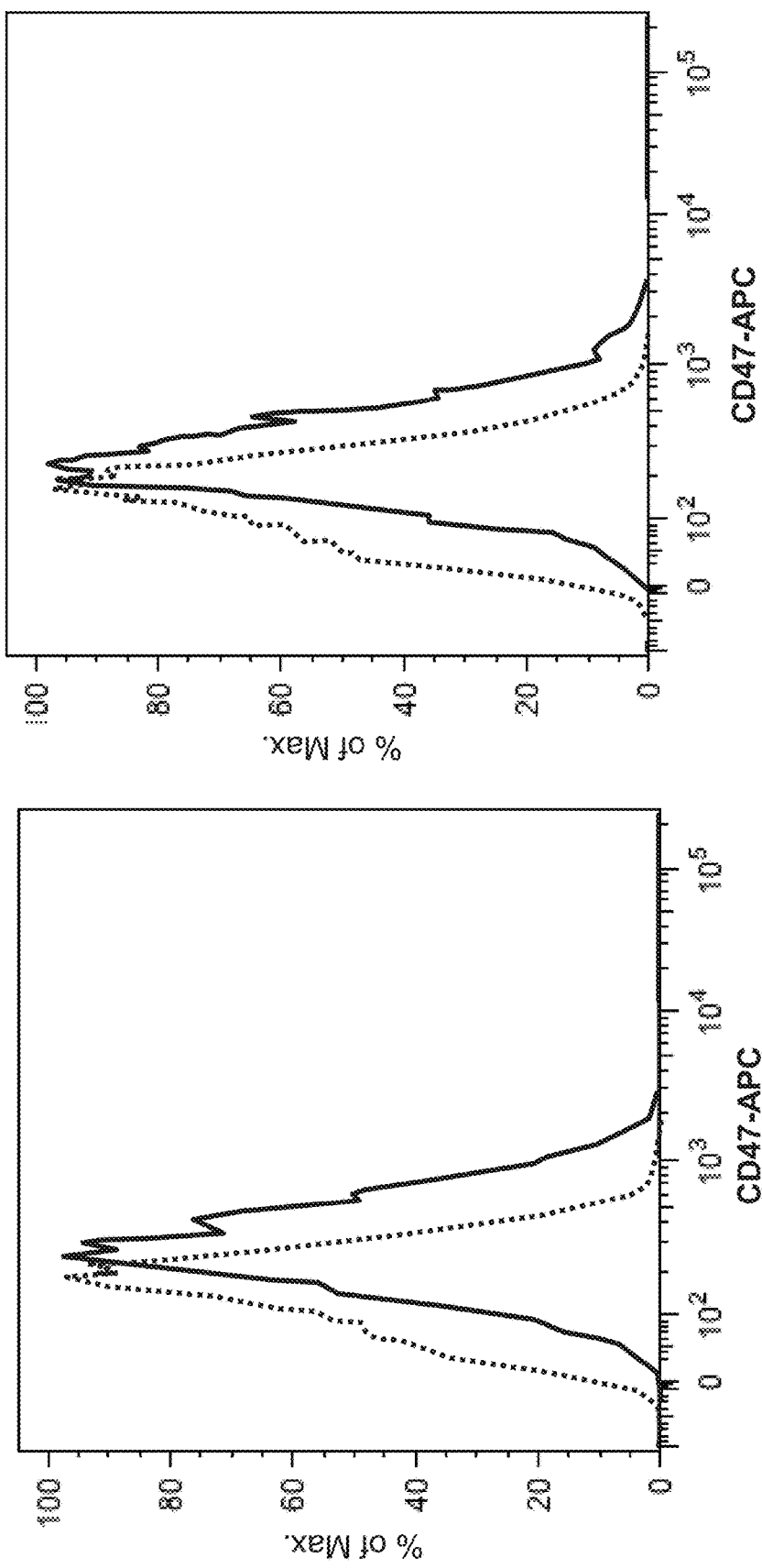

Infected and uninfected cells were isolated from mouse neonates infected with the Fr98-neurotropic mouse leukemia virus. FR98-infected cells expressed increased levels of CD47 compared to uninfected cells from the same animal (FIG. 2A-2B). This trend held true for multiple individual cell types that were isolated, demonstrating a general trend that infected cells express increased levels of CD47 compared to uninfected cells, regardless of cell type (FIG. 3A-3B).

Increased levels of CD47 were expressed by HIV-infected cells compared to uninfected cells (FIG. 4A-4D). PBMCs were isolated from 3 different people, and the cells underwent CD8-CD56-bead negative selection and stimulation with anti-CD3, anti-CD28 and IL-2 for 4 days.

Figure 5:
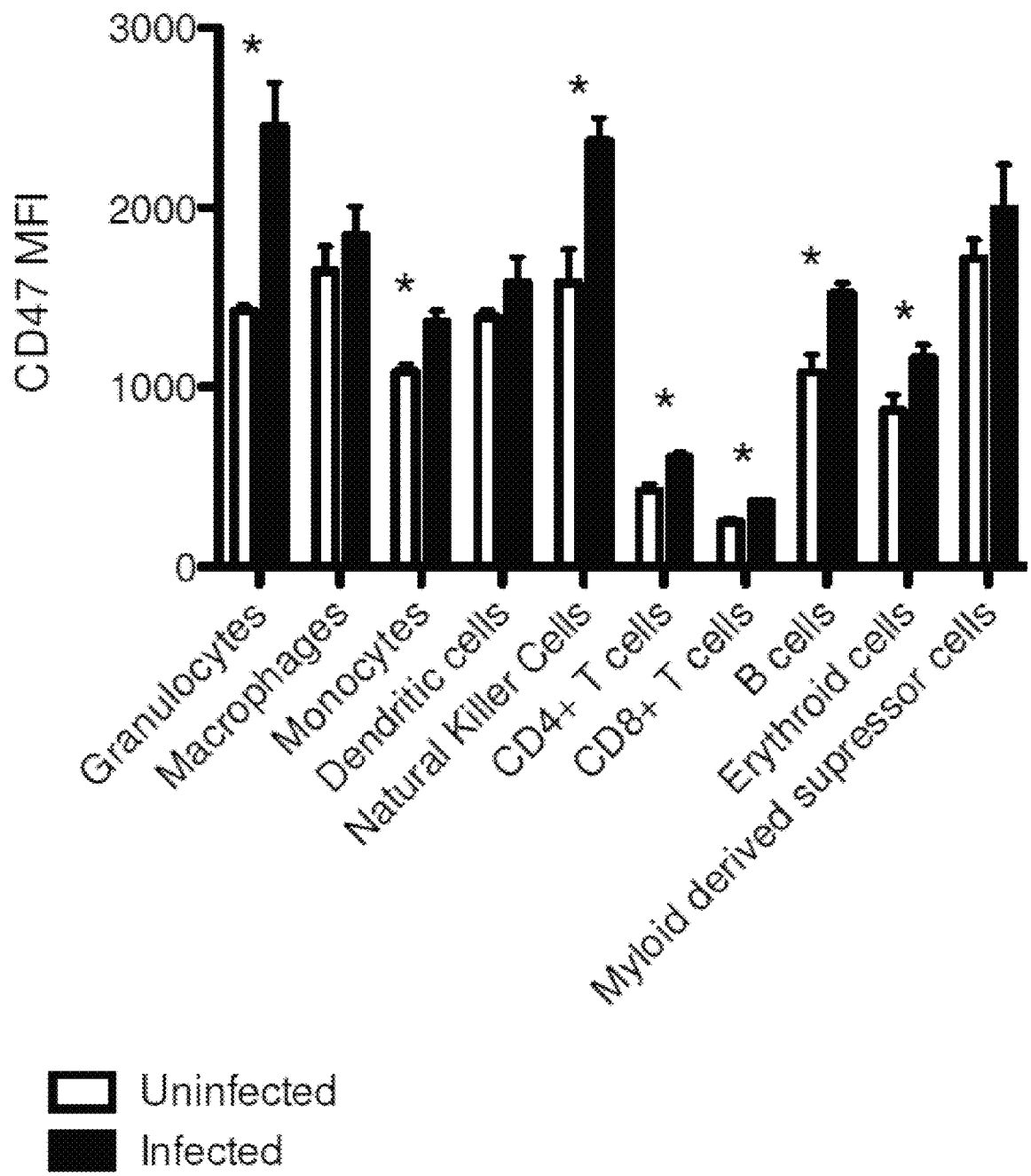
FIG. 5 demonstrates increased CD47 levels in La Crosse Virus infected cells compared to uninfected cells for a variety of different cell types (28 days post-infection of mice).

Increased levels of CD47 were expressed by a variety of different infected cell types isolated from mice 28 days following infection with the La Crosse Virus compared to uninfected cells (FIG. 5).

Figure 6A:
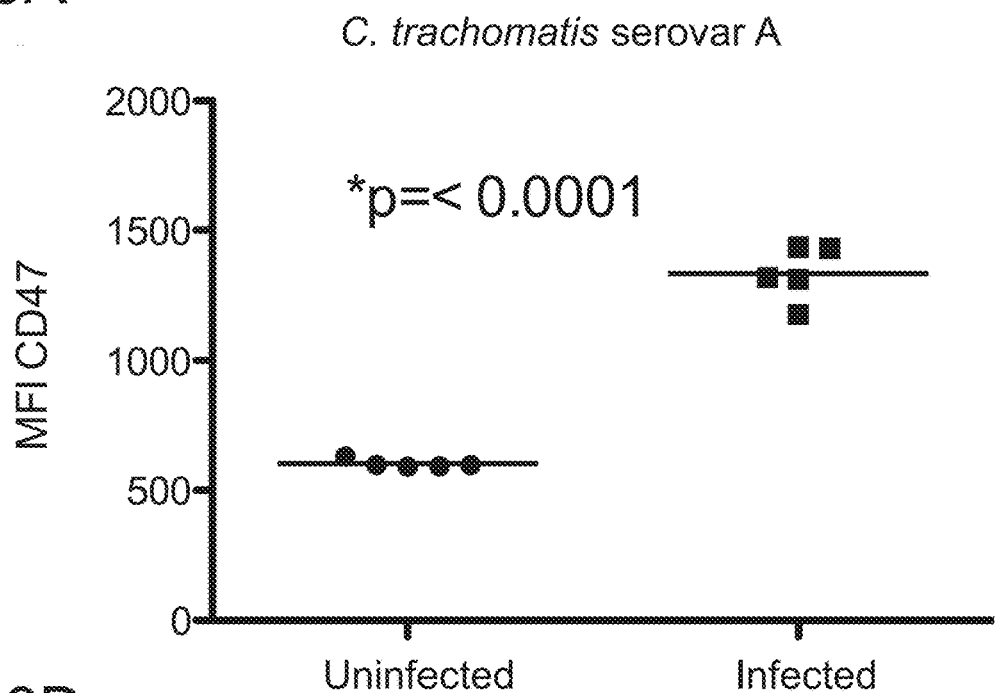
FIG. 6A-6B demonstrates an upregulation of CD47 in HeLa cells infected with *Chlamydia* serovar A, a strain with reduced macrophage tropism. CD47 expression was detected by staining with recombinant SIRPα-Fc fusion protein.
Figure 6B:
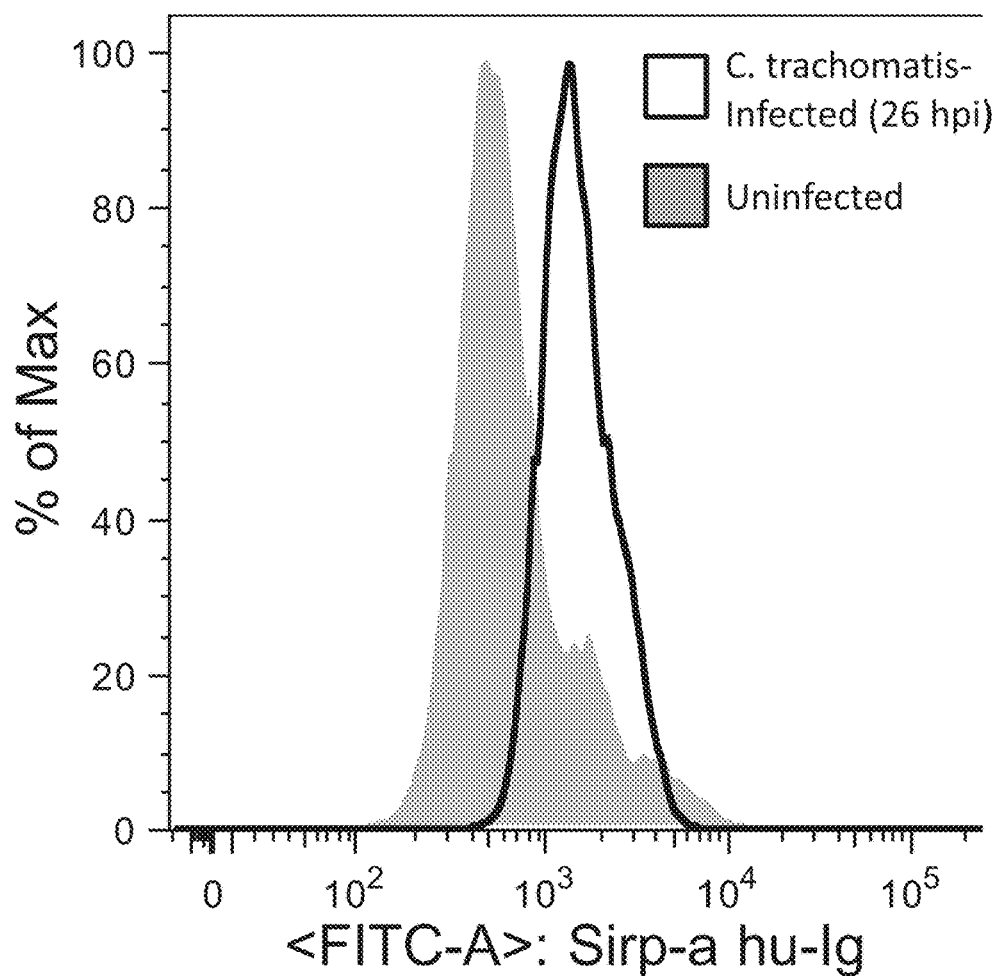

Increased levels of CD47 were expressed by HeLa cells infected with *Chlamydia trachomatis* serovar A (a bacterial pathogen) compared to uninfected cells (FIG. 6A-6B).

Based on the above findings, the binding of CD47 on a first cell to SIRPα on a second cell is expected to increase the phagocytosis of infected cells. To test this expectation, an anti-CD47 agent (the anti-CD47 antibody 5F9-hIgG4) was administered to mice (SCID-hu Thy/Liv) harboring an HIV infection.

As described in Stoddart et al. (Stoddart C A et al., PLoS One. 2007 Aug. 1; 2(7):e655), the SCID-hu mouse model, in which human lymphoid organs are implanted into severe-combined immunodeficient (SCID) mice, was designed to provide a small animal model for the study of human hematopoiesis (McCune, 1988, Science 241:1632-1639). These mice facilitated study of the pathogenesis of HIV-1 in human hematolymphoid organs and evaluation of anti-HIV-1 compounds in vivo. In this model, SCID mice are implanted with a variety of human fetal organs, including bone, liver, thymus, lymph node, and spleen. The fetal implants become tolerant of the mouse environment, and reciprocally, growth of the human tissue is permitted by the immunocompromised status of the recipient SCID mouse.

The SCID-hu Thy/Liv mouse, first reported by Namikawa et al. in 1990 (J Exp Med 172: 1055-1063,1990), is generated by co-implanting human fetal thymus and liver beneath the mouse kidney capsule. In a highly reproducible manner, these organs fuse, become vascularized, and grow into a stable organ termed "Thy/Liv," reaching a total mass of $100\text{-}300\times10^6$ human cells in 18 weeks. The Thy/Liv implant reproduces the differentiation, proliferation, and function of human hematopoietic progenitor cells derived from the fetal liver within the human thymus. The implants possess histologically normal cortical and medullary compartments that sustain multilineage human hematopoiesis for 6-12 months, generating a continuous source of CD4-expressing thymocytes that can serve as target cells for HIV-1 infection and replication. Importantly for a model of antiviral chemotherapy, 50-60 SCID-hu Thy/Liv mice can be made with tissues from a single fetal donor, and the Thy/Liv implant is amenable to experimental manipulation and infection with HIV-1. The Thy/Liv implants support viral replication after inoculation of HIV-1 by direct injection, and thymocyte depletion occurs with both molecular clones and clinical isolates of HIV-1 in 3-5 weeks. This depletion includes loss of $CD4^+CD8^+$ (double-positive, DP) immature cortical thymocytes and a decrease in the CD4/CD8 ratio in the thymic medulla.

The SCID-hu Thy/Liv mouse model of HIV-1 infection is considered in the art to be a useful platform for the preclinical evaluation of antiviral efficacy in vivo. This model of HIV is considered to be a highly reproducible mouse model that is likely to predict clinical antiviral efficacy in humans (Stoddart C A et al., PLoS One. 2007 Aug. 1; 2(7):e655).

An anti-CD47 agent (a humanized monoclonal antibody 5F9-hIgG4) was administered via intraperitoneal injection to SCID-hu Thy/Liv mice harboring a persistent HIV infection. An evaluation of the antiviral activity of the anti-CD47 agent is presented in FIG. 7A-7D, demonstrating the effectiveness of the methods of the invention.

The invention claimed is:

1. A method of treating a human subject infected with a retrovirus or lentivirus, the method comprising:
administering to the subject infected with a retrovirus or lentivirus, an anti-CD47 agent that reduces the binding of CD47 on a virus-infected cell to signal-regulatory protein alpha (SIRPα) on a phagocytic cell, at an effective dose for increasing the phagocytosis of the virus-infected cell, wherein the anti-CD47 agent is: (a) an anti-CD47 antibody, (b) an anti-SIRPα antibody that does not stimulate signaling through SIRPα, (c) a SIRPα polypeptide that specifically binds to CD47, or (d) a soluble CD47 polypeptide that specifically binds to SIRPα and does not stimulate signaling through SIRPα;
wherein phagocytosis of the virus-infected cells is increased.

2. The method of claim 1, wherein the virus is selected from HIV-1, HIV-2, HTLV, FIV, and SIV.

3. The method of claim 1, wherein the anti-CD47 agent is an anti-CD47 antibody.

4. The method of claim 3, wherein the anti-CD47 antibody is a fully human, humanized or chimeric antibody.

5. The method of claim 3 wherein the anti-CD47 antibody is an antibody fragment.

6. The method of claim 5, wherein the antibody fragment is: (a) Fab, Fab', Fab'-SH, F(ab')2 or Fv fragment or (b) a diabody.

7. The method of claim 1, wherein the anti-CD47 agent is an anti-SIRPα antibody that does not stimulate signaling through SIRPα.

8. The method of claim 7, wherein the anti-SIRPα antibody is a fully human, humanized or chimeric antibody.

9. The method of claim 1, wherein the anti-CD47 agent is a SIRPα-derived polypeptide that specifically binds to CD47.

10. The method of claim 9, wherein the SIRPα-derived polypeptide comprises at least the d1 domain of SIRPα with modified amino acid residues to increase affinity.

11. The method of claim 10, wherein the SIRPα-derived polypeptide is a fusion protein, optionally wherein the SIRPα-derived polypeptide is fused in frame with an immunoglobulin Fc region.

12. The method of claim 1, wherein the anti-CD47 agent is a soluble CD47 polypeptide that specifically binds to SIRPα and does not stimulate signaling through SIRPα.

13. A method of treating a human subject infected with a retrovirus or lentivirus, the method comprising:
administering to the subject infected with a retrovirus or lentivirus, a combination of (i) an anti-CD47 agent that reduces the binding of CD47 on a virus-infected cell to signal-regulatory protein alpha (SIRPα) on a phagocytic cell, at an effective dose for increasing the phagocytosis of the virus-infected cell; and (ii) an antiviral agent, wherein the anti-CD47 agent is: (a) an anti-CD47 antibody, (b) an anti-SIRPα antibody that does not stimulate signaling through SIRPα, (c) a SIRPα polypeptide that specifically binds to CD47, or (d) a soluble CD47 polypeptide that specifically binds to SIRPα and does not stimulate signaling through SIRPα;

wherein phagocytosis of the virus-infected cell is increased.

14. The method of claim 13, wherein the virus is selected from HIV-1, HIV-2, HTLV, FIV, and SIV.

15. The method of claim 13, wherein the antiviral agent is a cytokine.

16. The method of claim 15, wherein the cytokine is one or more of interferon γ, tumor necrosis factor α, and interleukin 12.

17. The method of claim 13, wherein the antiviral agent is acyclovir or gancyclovir.

18. The method of claim 13, wherein the virus is selected from HIV-1, HIV-2, HTLV, FIV, and SIV.

19. The method of claim 13, wherein the anti-CD47 agent is an anti-CD47 antibody.

20. The method of claim 19, wherein the anti-CD47 antibody is a fully human, humanized or chimeric antibody.

21. The method of claim 19 wherein the anti-CD47 antibody is an antibody fragment.

22. The method of claim 21, wherein the antibody fragment is: (a) Fab, Fab', Fab'-SH, F(ab')2 or Fv fragment or (b) a diabody.

23. The method of claim 13, wherein the anti-CD47 agent is an anti-SIRPα antibody that does not stimulate signaling through SIRPα.

24. The method of claim 23, wherein the anti-SIRPα antibody is a fully human, humanized or chimeric antibody.

25. The method of claim 13, wherein the anti-CD47 agent is a SIRPα-derived polypeptide that specifically binds to CD47.

26. The method of claim 25, wherein the SIRPα-derived polypeptide comprises at least the d1 domain of SIRPα with modified amino acid residues to increase affinity.

27. The method of claim 26, wherein the SIRPα-derived polypeptide is a fusion protein, optionally wherein the SIRPα-derived polypeptide is fused in frame with an immunoglobulin Fc region.

28. The method of claim 13, wherein the anti-CD47 agent is a soluble CD47 polypeptide that specifically binds to SIRPα and does not stimulate signaling through SIRPα.

* * * * *

SEQUENCE LISTING

```
<160> NUMBER OF SEQ ID NOS: 3

<210> SEQ ID NO 1
<211> LENGTH: 124
<212> TYPE: PRT
<213> ORGANISM: Homo sapiens

<400> SEQUENCE: 1

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn
        115                 120

<210> SEQ ID NO 2
<211> LENGTH: 18
```

```
<212> TYPE: PRT
<213> ORGANISM: Artificial Sequence
<220> FEATURE:
<223> OTHER INFORMATION: Sythetic polypeptide sequence

<400> SEQUENCE: 2

Met Trp Pro Leu Val Ala Ala Leu Leu Leu Gly Ser Ala Cys Cys Gly
1               5                   10                  15

Ser Ala

<210> SEQ ID NO 3
<211> LENGTH: 142
<212> TYPE: PRT
<213> ORGANISM: Homo sapiens

<400> SEQUENCE: 3

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn
        130                 135                 140
```